United States Patent [19]

Kudo et al.

[11] Patent Number: 5,279,788

[45] Date of Patent: Jan. 18, 1994

[54] STERILIZER FOR SEALED CONTAINER UTILIZING MICROWAVE

[75] Inventors: Minoru Kudo; Toshiyasu Ehara, both of Saitama; Kenichi Iijima, Isezaki; Washiro Honda; Katsumi Shimizu, both of Honjo, all of Japan

[73] Assignees: Eisai Co., Ltd., Tokyo; Micro Denshi Co., Ltd., Saitama, both of Japan

[21] Appl. No.: 824,003

[22] Filed: Jan. 22, 1992

[30] Foreign Application Priority Data

Jan. 24, 1991 [JP] Japan .................................. 3-024084
Dec. 16, 1991 [JP] Japan .................................. 3-352635

[51] Int. Cl.⁵ .................................................. A61L 2/00
[52] U.S. Cl. ...................................... 422/21; 422/307; 219/10.55 A
[58] Field of Search .................. 422/21, 25, 292, 307; 219/10.55A, 10.61R

[56] References Cited

U.S. PATENT DOCUMENTS

| | | | |
|---|---|---|---|
| 4,599,216 | 7/1986 | Rohrer et al. | 422/21 |
| 4,614,514 | 9/1986 | Carr et al. | 422/21 |
| 4,822,967 | 4/1989 | Kumagami et al. | 422/307 |
| 4,870,236 | 9/1989 | Berggren | 219/10.55 A |
| 4,908,492 | 3/1990 | Okamoto et al. | 219/10.55 A |
| 5,061,443 | 10/1991 | Iijima et al. | 422/21 |
| 5,132,504 | 7/1992 | Iijima | 422/21 |

*Primary Examiner*—James C. Housel
*Assistant Examiner*—Lien Tran
*Attorney, Agent, or Firm*—Griffin Butler

[57] ABSTRACT

In the microwave oven of square waveguide type or coaxial tube type, the waveguide or inner conductor of the tube type is gradually declined from the inlet toward the outlet of the oven. A top slot is provided so that containers may be moved along the slot with their bottom portions being received in the oven and the contents heat sterilized. There is laid on a bottom surface of the oven a support rail for the bottoms of the containers, and this rail is gradually thickened from the inlet toward the outlet. More preferably, two or more such microwave ovens may be serially connected and the containers may be moved therethrough to heat sterilize medical fluids within each container in a step-wise manner.

22 Claims, 15 Drawing Sheets

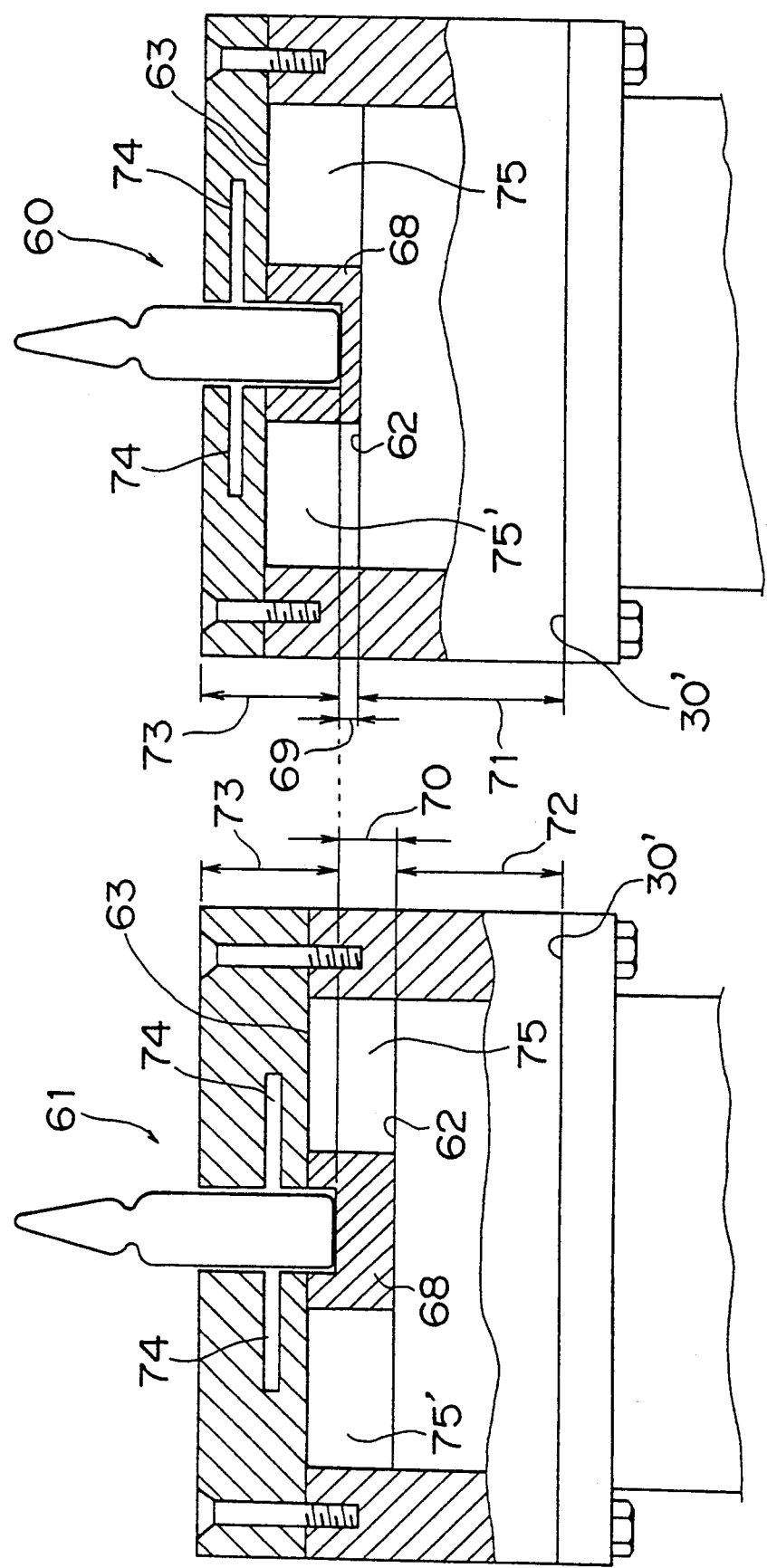

STERILIZER FOR SEALED CONTAINER UTILIZING MICROWAVE

BACKGROUND OF THE INVENTION

This invention relates to an apparatus utilizing microwave to heat-sterilize a sealed container filled with medical fluid and particularly to a microwave oven of coaxial tube type or waveguide type for such purpose.

The sealed container, for example, an ampoule filled with medical fluid such as injection medicine is conventionally subjected to a sterilizing treatment during its manufacturing process.

As means for sterilization, those employing microwave or auto clave are well known.

The means utilizing the microwave is well known, for example, from Japanese Patent Application Disclosure Gazette No. 1973-59976 entitled "Method and apparatus for sterilization of medical fluid contained within ampoule", Japanese Patent Application Disclosure Gazette No. 1973-104381 entitled "Method and apparatus for sterilization of ampoule filled with liquid" and Japanese Patent Application Disclosure Gazette No. 1975-38985 entitled "Sterilizer for ampoule filled with liquid".

The applicant of this application also has already proposed "Apparatus and method for sterilization of sealed container utilizing microwave" in U.S. Pat. No. 5,061,443 and Japanese Patent Application No. 1989-147666 (U.S. patent application Ser. No. 07/530414, U.S. Pat. No. 5,132,504).

The microwave heater of oven type is also well known, for example, from U.S. Pat. No. 4,687,895.

However, it has been difficult for the heating means utilizing the auto clave to control the temperature of individual sealed containers and such heating means sometimes has encountered a problem of medical fluid decomposition. Furthermore, it has been impossible for such heating means to realize a continuous process of manufacturing.

The conventional heating means utilizing the microwave has been inconvenient in that the microwave can not be efficiently absorbed by the sealed container and, to compensate for this, it has been necessary to increase output of the microwave oscillator. In addition, the well known heating means utilizing the microwave has been disadvantageous also in that the sealed container of a large volume can not be adequately sterilized. More specifically, most of such conventional apparatuses have been provided with a single microwave irradiation oven and, therefore, the output of the microwave oscillator for this single oven has had to be increased to heat the sealed container of a large volume. As a result, an extremely intense microwave energy has been concentrated onto the sealed container passing by the oscillator and there has been an anxiety that the temperature of medical fluid could not be controlled.

Specifically, the intense microwave energy is absorbed by the medical fluid contained within the sealed container, leading to a sudden rise of the temperature thereof, and it becomes difficult to control the temperature to a desired level. There have been further problems such as rupture of the container due to a sudden pressure rise within the container and damage of the container due to electric short caused by a high electrolytic intensity of the microwave between the sealed container and the medical fluid contained therewithin.

It has been impossible for the conventional microwave heating apparatus of oven type not only to irradiate a plurality of sealed containers evenly with the microwave but also to achieve a local irradiation and, accordingly, no stable sterilization has been expectable. Particularly in the well known apparatus disclosed by U.S. Pat. No. 4,687,895 which is adapted to convey objects to be heated into respective cavities and to heat them within the respective cavities, there must be provided partition between each pair of adjacent cavities and there must be provided a mechanism used to open and shut these partitions. With a consequence, the mechanical construction is necessarily complicated and heating must be stopped everytime the partitions are opened. Such requirement results in a large heat loss and makes a continuous heating process impossible. The apparatus disclosed by the above-mentioned U.S. Patent has been unpractical for heat-sterilization of ampoule, vial or the like which unexceptionally requires a high accuracy of heat-sterilization, because this apparatus of prior art can not control heating of such object with a desired accuracy.

SUMMARY OF THE INVENTION

Accordingly, it is an object of the invention to provide a microwave irradiation oven of so-called coaxial tube type containing an inner conductor embedded therein to so improve the propagation of the microwave that an absorption efficiency may be appropriately varied from an inlet side toward an outlet side of the microwave irradiation oven, a dose of microwave irradiation may be kept substantially constant and the temperature may rise at a constant ratio to achieve a substantially even sterilization occurring without a sudden rise of the temperature.

The object set forth above is achieved, in accordance with an aspect of the invention, by a sterilizer for a sealed container utilizing microwave comprising a microwave oven of so-called coaxial tube type containing an inner conductor embedded therein, wherein the inner conductor is formed in a top thereof with a slot so that the sealed container may be moved along said slot with its bottom portion being received in said slot and the content of said sealed container may be heat-sterilized.

Preferably, a degree of coupling between the microwave and the medical fluid contained within the seal container gradually increases from the outlet side toward the inlet side of the microwave oven at a constant ratio.

Said degree of coupling is optimally varied by gradually declining the inner conductor of said microwave oven from the inlet side toward the outlet side of the oven so as to define a slope and laying a rail on the top of the inner conductor to support the bottom of the sealed container, wherein said rail is gradually thickened from the inlet side toward the outlet side of the oven.

Such technical measure allows the microwave to be efficiently absorbed by the bottom of the sealed container and causes a convection within the sealed container, thus reducing a temperature difference between upper and lower portions of the medical fluid so that said medical fluid may be evenly and adequately sterilized with a relatively low output of the microwave oscillator.

The unique measure that the inner conductor is sloped and thereby the absorption efficiency is gradually varied from the inlet side toward the outlet side of the oven allows the dose of microwave irradiation to be kept constant and allows the temperature to rise at a constant ratio.

Formation of a groove in the rail to support the bottom of the sealed container allows the sealed container to be stably conveyed, on one hand, and facilitates maintenance of the equipment, on the other hand, because, even if the glass container is broken during its conveyance, the removing of pieces of the broken glass container can be easily done.

It is another object of the invention to sterilize the content of the sealed container without breakage thereof by irradiating the sealed container with relatively feeble microwave instead of concentrated intense microwave.

This object is achieved, in accordance with another aspect of the invention, by continuously moving the sealed container through two or more serially connected microwave ovens and adjusting a dose of microwave irradiation to a level lower than the case in which a single microwave oven is used to heat the sealed container.

Such technical measure eliminates anxieties that the sealed container might be concentrally irradiated with unacceptably intense microwave and the container might be broken due to such intense microwave, because the content of the sealed container is stepwise heated through two or more serially connected microwave ovens. Additionally, such arrangement allows the sterilizer to be made compact.

Furthermore, the thickness variation of the rail from the inlet side toward the outlet side of the oven allows the oven's depth to be kept constant and facilitates connection of two or more ovens.

BRIEF DESCRIPTION OF THE DRAWINGS

The above and other objects of the invention will be seen by reference to the description taken in connection with the accompanying drawings, in which:

FIG. 5 is a plan view showing a relationship between a bucket 5 and an ampoule a;

FIG. 6 is a front view showing the bucket of FIG. 5 as holding the rail 7 between;

FIG. 18 is a sectional view showing an inlet side of the square waveguide type microwave oven of FIG. 17 taken along a line E—E; and FIG. 19 is a sectional view showing an outlet side of the square waveguide type microwave oven of FIG. 17 taken along a line F—F.

DETAILED DESCRIPTION OF THE INVENTION

An embodiment of the invention will be described in reference with the accompanying drawings.

Figure 1:
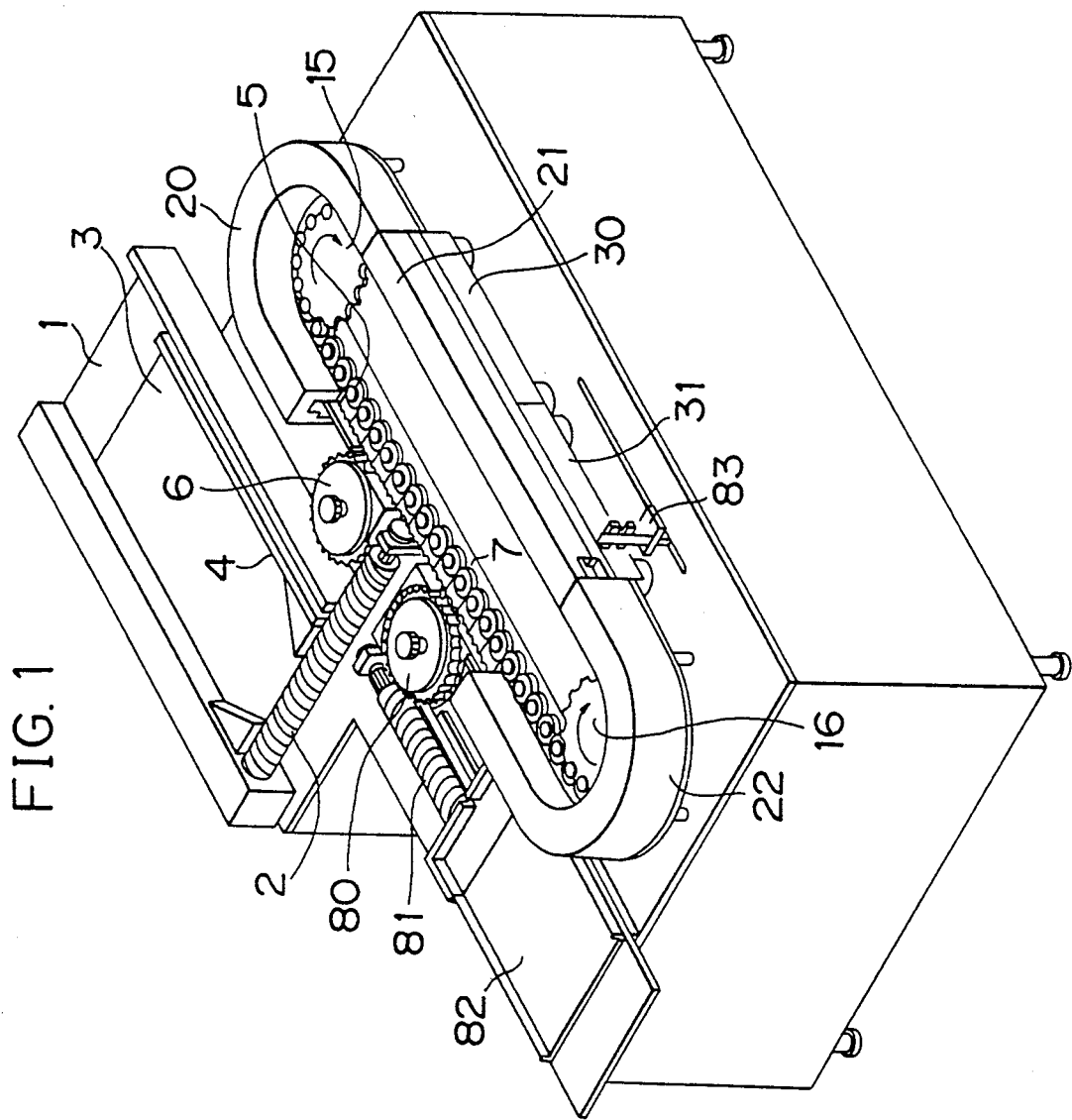
FIG. 1 is a perspective view exemplarily showing a microwave heat sterilizer constructed according to this invention.
Figure 2:
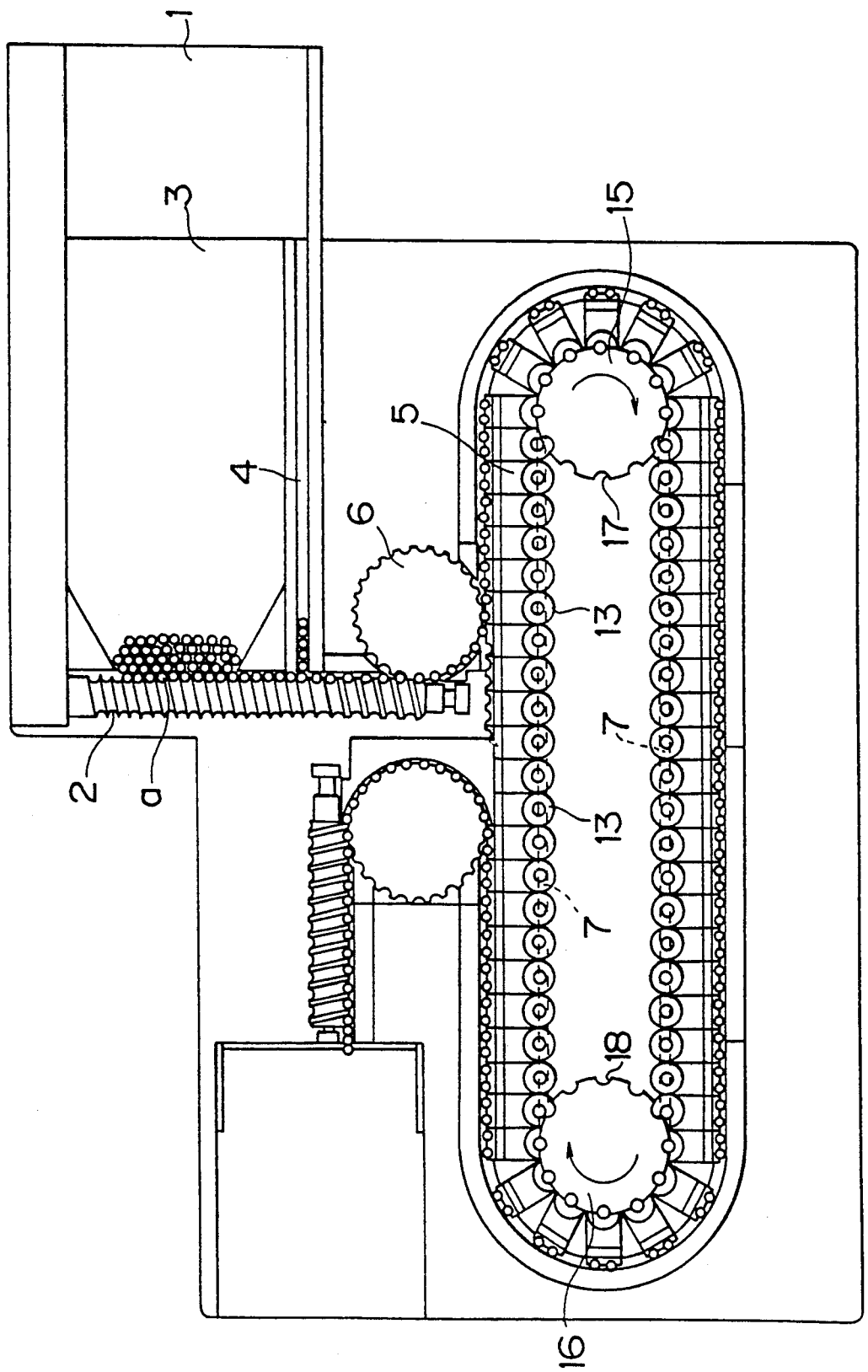
FIG. 2 is a plan view showing the sterilizer of FIG. 1 with casings for preheating, hot air blasting and heat insulation having been removed.

It should be understood here that the invention is not limited to this embodiment in the form of ampoule but can be applied to the sealed container of the other types such as vial or bottle. FIG. 1 and FIG. 2 are perspective and plan views, respectively, of the sterilizer of the invention. Referring to these figures, a hopper 1 is equipped with a conveyor 3 used to supply ampoules a to a screw 2. A mechanism 4 assures that the ampoules a can be reliably supplied even when they would not be properly engaged with the screw 2. Adjacent a forward end of the screw 2, there is provided a star wheel 6 serving to take the ampoules a out from the screw 2 and to supply them to a bucket 5 of the sterilizer.

Figure 3:
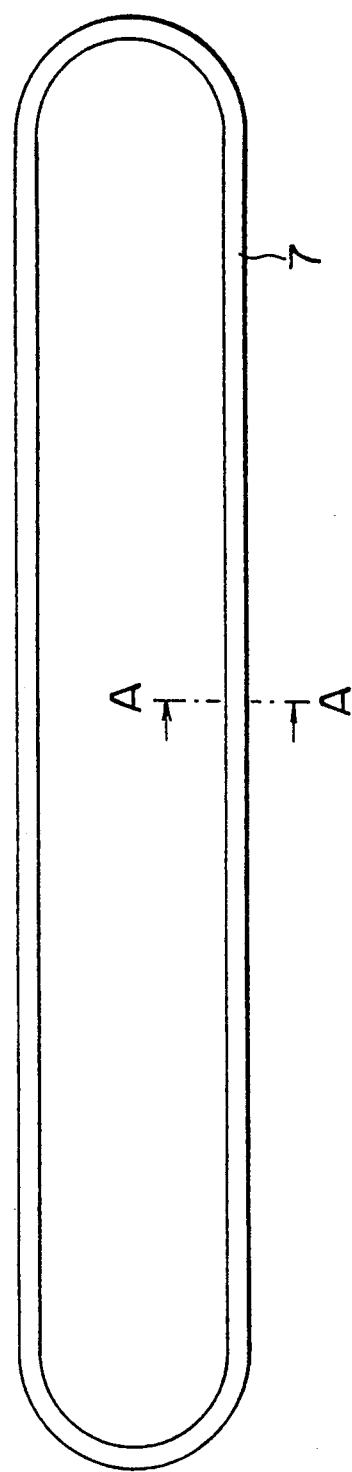
FIG. 3 is a plan view of a rail used in the sterilizer of FIG. 1.
Figure 4:
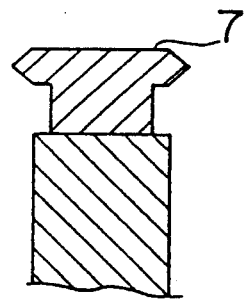
FIG. 4 is a sectional view taken along a line A—A in FIG. 3.

Within the sterilizer generally of an elliptical configuration, a correspondingly elliptical bucket rail 7 as shown by FIG. 3 is laid. Top of the rail 7 has a cross-section laterally widened as seen in FIG. 4.

Figure 5:
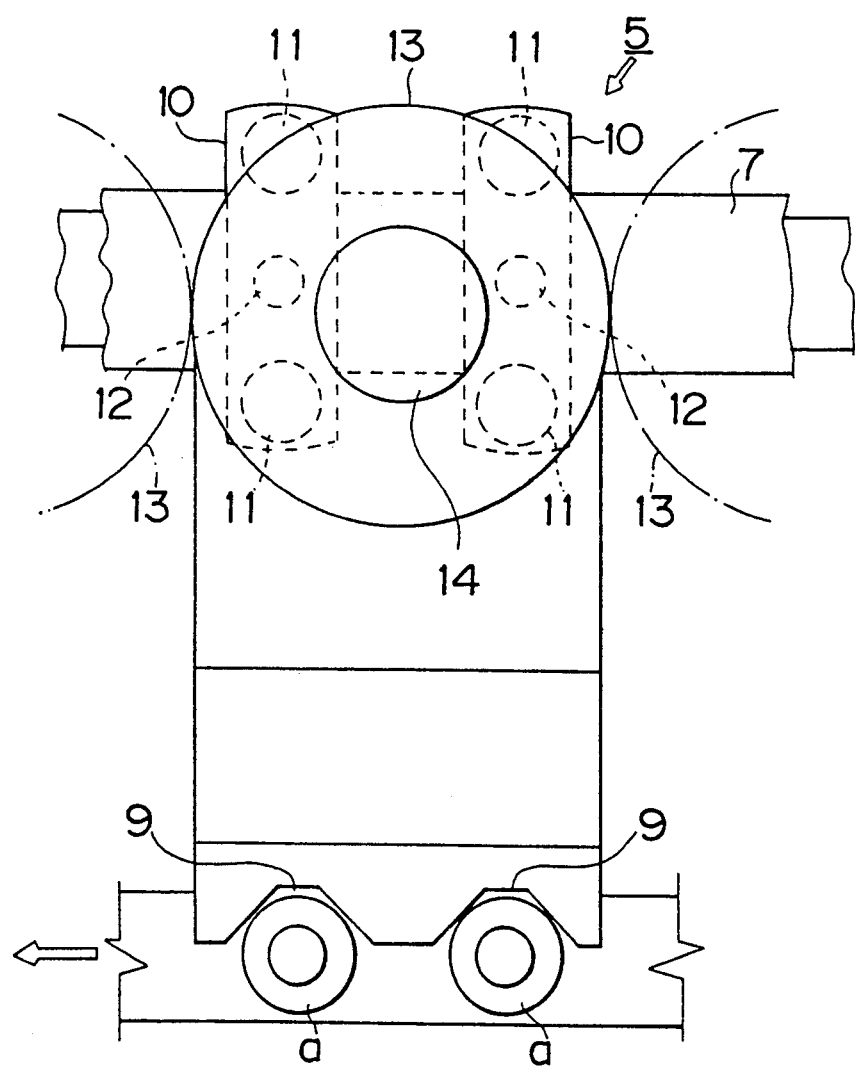
Figure 6:
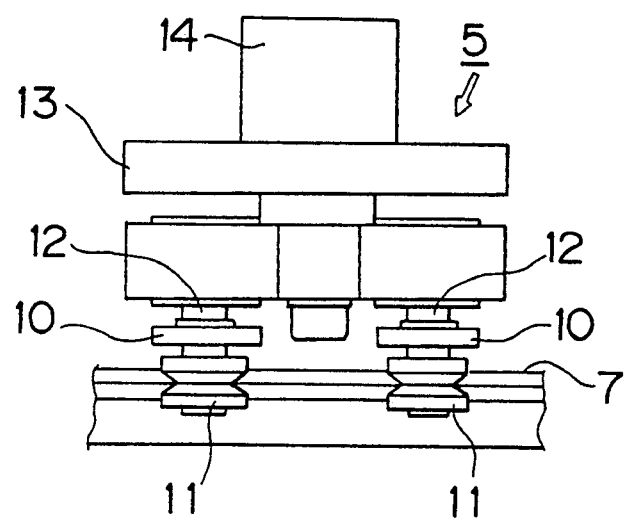
Figure 7:
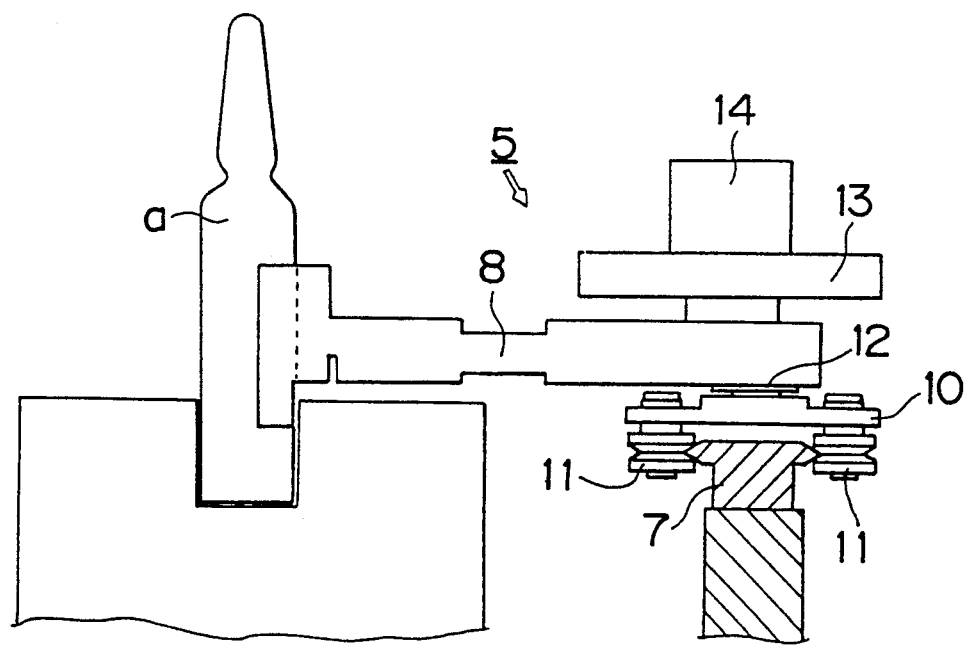
FIG. 7 is a side view showing the bucket of FIG. 5.

The bucket 5 which is movable on the rail 7 is of a configuration as shown by FIG. 5 through 7. More specifically, a forward end of a bucket arm 8 is formed with a pair of recesses 9 adapted to hold the ampoules a and a base of said arm 8 is provided on its underside with a pair of members 10 each carrying a pair of rollers 11 on its longitudinally opposite ends. Said members 10 are rotatably supported on shafts 12, respectively, projecting downward from the underside of said bucket arm 8. The rollers 11 are engaged with the rail 7 from both sides so that the bucket arm 8 may smoothly move along the rail 7.

The base of the bucket arm 8 carries on its top a disc 13 is centrally provided with a projection 14.

The buckets 5 are mounted on the rail 7 so as to be arranged in an elliptical array along the rail 7 with said rollers 11 being in engagement with the rail 7 from both sides as shown by FIG. 7 and the discs 13 of the adjacent buckets 5 being in contact with each other as shown by FIG. 2. Rotation of sprockets 15, 16 provided on laterally opposite sides of the sterilizer causes the buckets 5 of which the central projections 14 on the discs 13 engaged with circumferential grooves 17, 18 of the respective sprockets 15, 16 to be moved so that, as the buckets 5 successively pass the sprockets 15, 16, the discs 13 of the respective buckets 5 push one another and, consequently, all the buckets 5 on the rail 7 are moved clockwise along the rail 7.

Referring to FIG. 1, reference numerals 20, 21 and 22 designate casings for preheating, hot air blasting and heat insulating, respectively.

Figure 8:
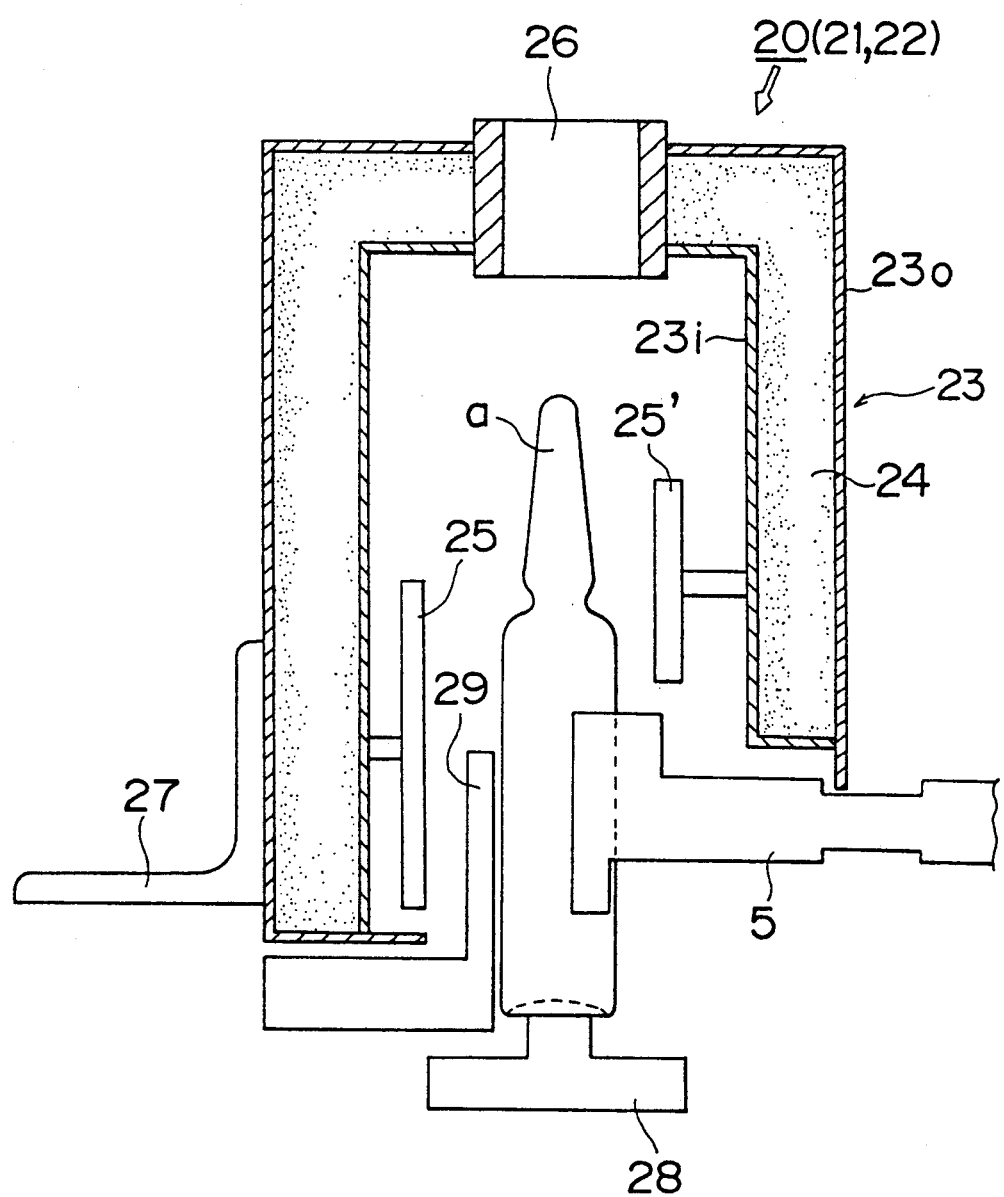
FIG. 8 is a sectional view showing a relationship of the bucket 5 with the casings for preheating, hot air blasting and heat insulation.

These casings have an inner construction common to them as shown by FIG. 8. The casing having a gate-shaped cross-section itself 23 is filled with a heat insulator 24 between its outer wall 23o and inner wall 23i. Within the casing itself 23, there are provided a pair of infrared heaters 25, 25' so as to be opposed to each other across the ampoules a. The casing itself 23 is additionally provided at the top thereof with an opening 26 through which a stream of air heated by a heater (not shown) is blast into the casing.

In this embodiment, the infrared heaters 25, 25' are vertically offset so that both a head of the ampoule a filled with no medical fluid and an intermediate potion of the ampoule a filled with medical fluid may be evenly preheated.

A preheating temperature of these infrared heaters 25, 25' is detected by suitable means such as a thermocouple and correspondingly controlled for each casing. Use of the infrared heaters allows a wave-length of 4 to 8 microns substantially unreflected by borosilicate glass to be emitted, thereby improving a heat absorptivity and minimizing a temperature unevenness for each ampoule a.

Referring to FIG. 8 reference numeral 27 designates an angle used to fasten the casing itself 23 onto a top surface of the sterilizer, reference numeral 28 designates a support rail serving to support the ampoules a conveyed by the buckets 5 from bottoms thereof and reference numeral 29 designates a guide used to protect the ampoules a against falling sideways.

Figure 9:
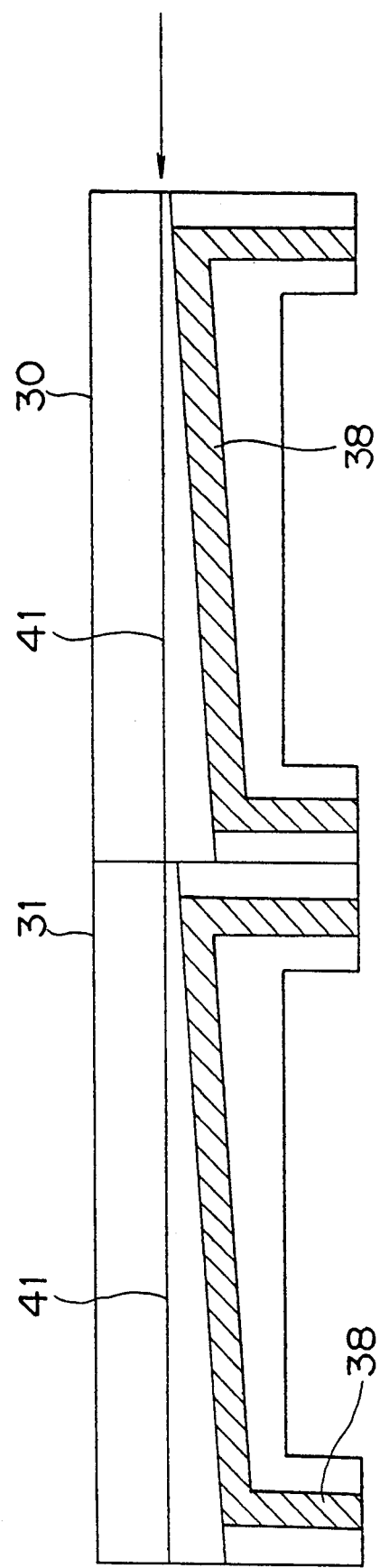
FIG. 9 is a sectional view of serially connected coaxial tube type microwave ovens.

Now referring to FIG. 1, the casing for hot air blasting 21 includes along its lower portion serially connected microwave ovens 30, 31 which have constructions identical to each other. One example of these serially connected microwave ovens is shown by FIG. 9.

The microwave oven used for the invention is classified, depending on its manner of irradiation, into a coaxial tube type and a waveguide type having specific constructions, respectively, as well be described below.

(A) COAXIAL TUBE TYPE

Figure 10:
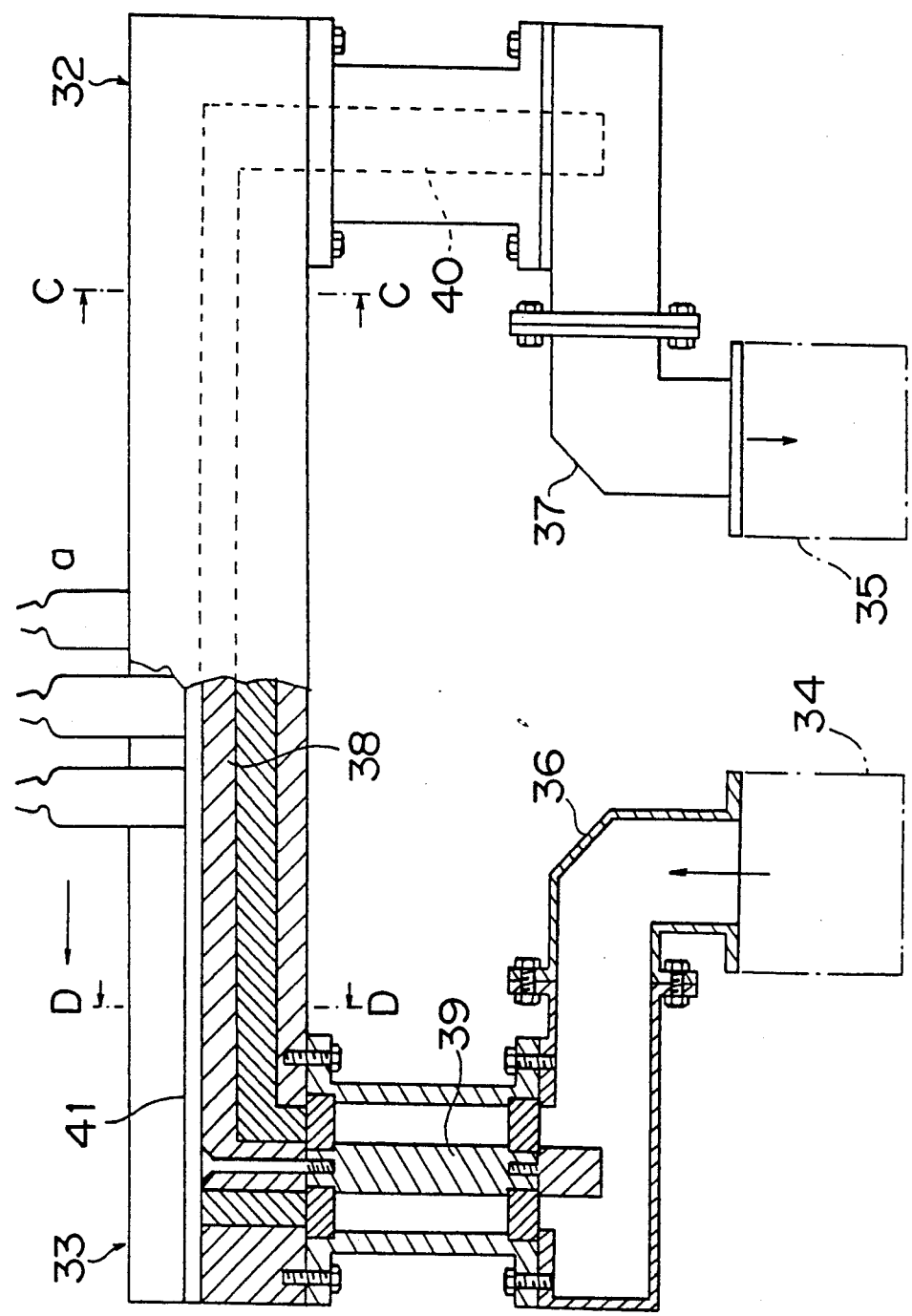
FIG. 10 is a front view showing, partially in a section, one of the coaxial tube type microwave ovens of FIG. 9.

Referring to FIG. 10, reference numeral 32 designates an inlet side for the ampoules a into the oven and reference numeral 33 designates an outlet side for the ampoules a from the oven. The ampoules a conveyed by the buckets 5 move in a direction as indicated by an arrow in FIG. 10 from right hand to left hand as viewed in FIG. 10. There are provided below the microwave oven 30 and a microwave oscillator 34 which is connected by a waveguide 36 to the outlet side 33 of said microwave oven 30 and a microwave absorber 35 which is connected by a waveguide 37 to the inlet side 32 of the microwave oven 30. An inner conductor 38 is embedded in the microwave oven 30 and dependant portions 39, 40 of said inner conductor 38 extending downward from longitudinally opposite ends thereof are received into the waveguides 36, 37, respectively, so that the microwave generated in the microwave oscillator 34 is propagated by the inner conductor in a direction from the outlet side 33 to the inlet side 32 of the microwave oven 30. The direction in which the microwave is propagated is opposite to the direction in which the ampoules a are moved.

Figure 13:
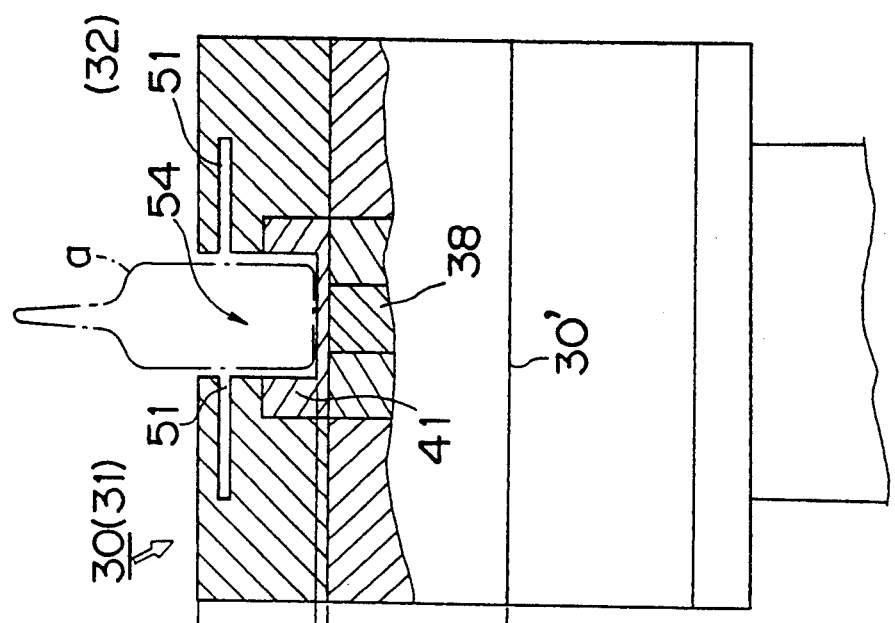
FIG. 13 is a sectional view showing an inlet side of the coaxial tube type microwave oven of FIG. 10 taken along a line C—C in FIG. 10.
Figure 14:
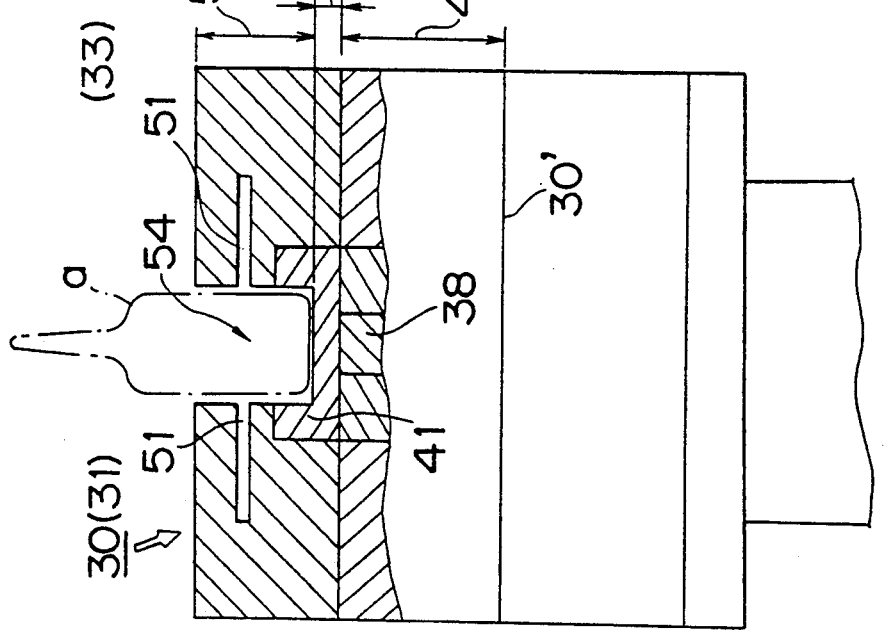
FIG. 14 is a sectional view showing an outlet side of the coaxial tube type microwave oven of FIG. 10 taken along a line D—D in FIG. 10.
Figure 15:
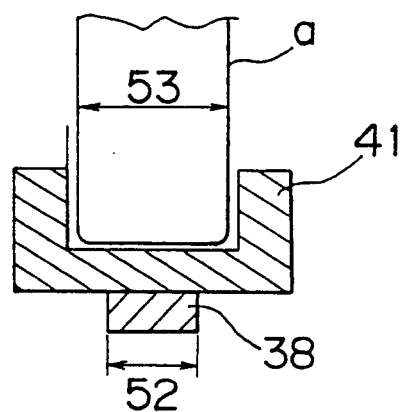
FIG. 15 is a sectional view showing a relation between a width of an inner conductor provided in the coaxial tube type microwave oven and a diameter of the ampoule.

FIG. 13 and 14 are sectional views of the microwave oven 30 as mentioned above, and it will be apparent that the microwave oven 30 is formed in its top surface with a slot 54. With the bottoms of ampoules a being received into this slot 54, the ampoules a are conveyed by the buckets 5 within the microwave oven 30 while they are irradiated with microwave.

Figure 11:
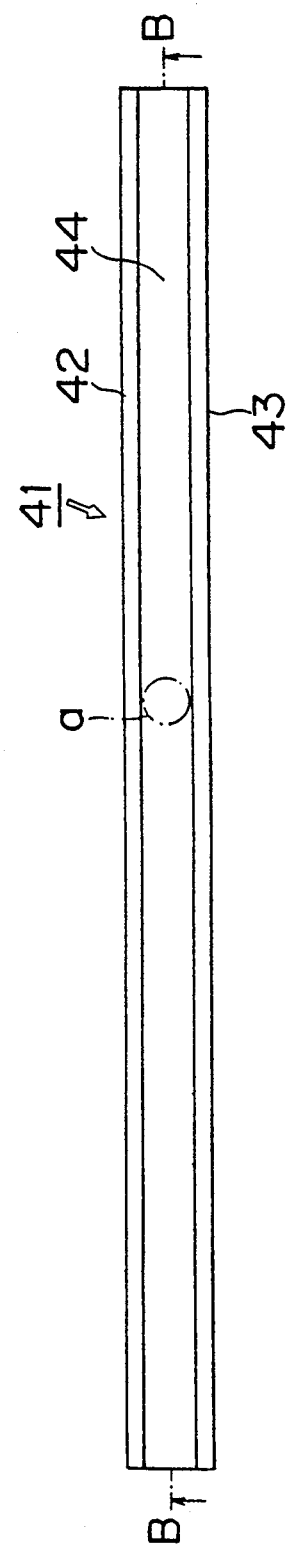
FIG. 11 is a plan view showing a rail 41 laid on the bottom of the coaxial tube type microwave oven.
Figure 12:
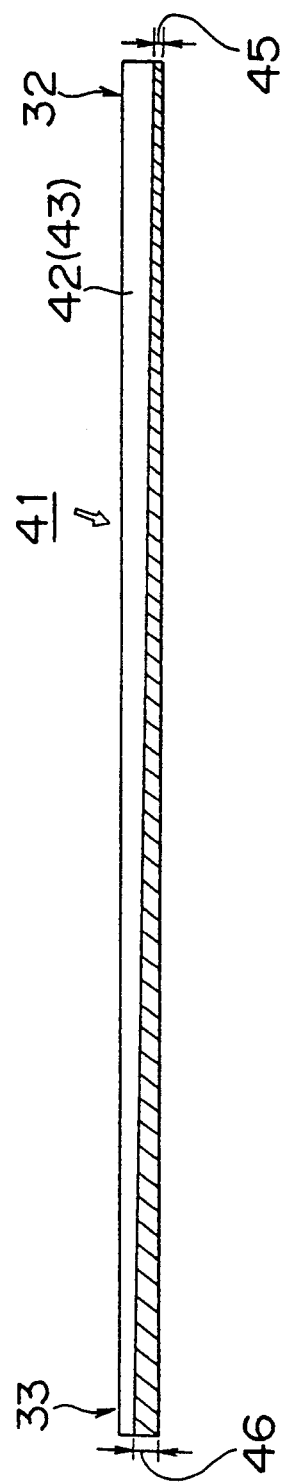
FIG. 12 is a sectional view taken along a line B—B in FIG. 11.

There is laid a rail 41 above the inner conductor 38. As is best seen in FIG. 11 and 12, the rail 41 has a U-shaped cross-section of which the legs 42, 43 define a groove 44 therebetween so that the ampoules a may move with their bottom in contact with a floor of the groove 44. The floor of the groove 44 is relatively thin at the inlet side 32 as shown by a thickness 45 and gradually thickened toward the outlet side 33 of the oven 30 at a given ratio, as shown by a thickness 46. While the instant embodiment employs the rail 41 made of thermoplastic polymethylpentene (TPX; manufactured by Mitsui Petrochemical Industries, Ltd.), such rail 41 made of any other material such as Teflon which is heat resisting and microwave-unabsorbable may also be employed.

The microwave oven 30 of coaxial tube type as has been described above presents a cross-sectional configuration as shown by FIG. 13 on its inlet side and a cross-sectional configuration as shown by FIG. 14 on its outlet side. As shown, the oven 30 has a height 48 as measured from the oven's bottom 30' to the inner conductor 38 on the inlet side 32 and this height is larger than a corresponding height 49 on the outlet side 33 of the oven 30. As has previously been explained in reference with FIG. 12, the rail 41 has the thickness 45 on the inlet side 32 less than thickness 46 on the outlet side 33 of the oven 30. In this manner, the slope of the inner conductor 38 and the thickness variation of the rail 41 offset each other so that the microwave oven 30 can provide a uniform depth 50 over an extent spanning from the inlet side 32 to the outlet side 33 of the oven 30 and thereby assure a horizontal surface along which the ampoules a move (see FIG. 9).

As best seen in FIGS. 13 and 14, there is provided laterally of the slot 54 a choke 51 serving to absorb the microwave which otherwise might escape upward along the ampoules a. In addition, the inner conductor 38 has a width 52 smaller than a diameter 53 of each ampoule a so that the bottom of each ampoule a can be efficiently irradiated with the microwave.

(B) WAVEGUIDE TUBE TYPE

Figure 17:
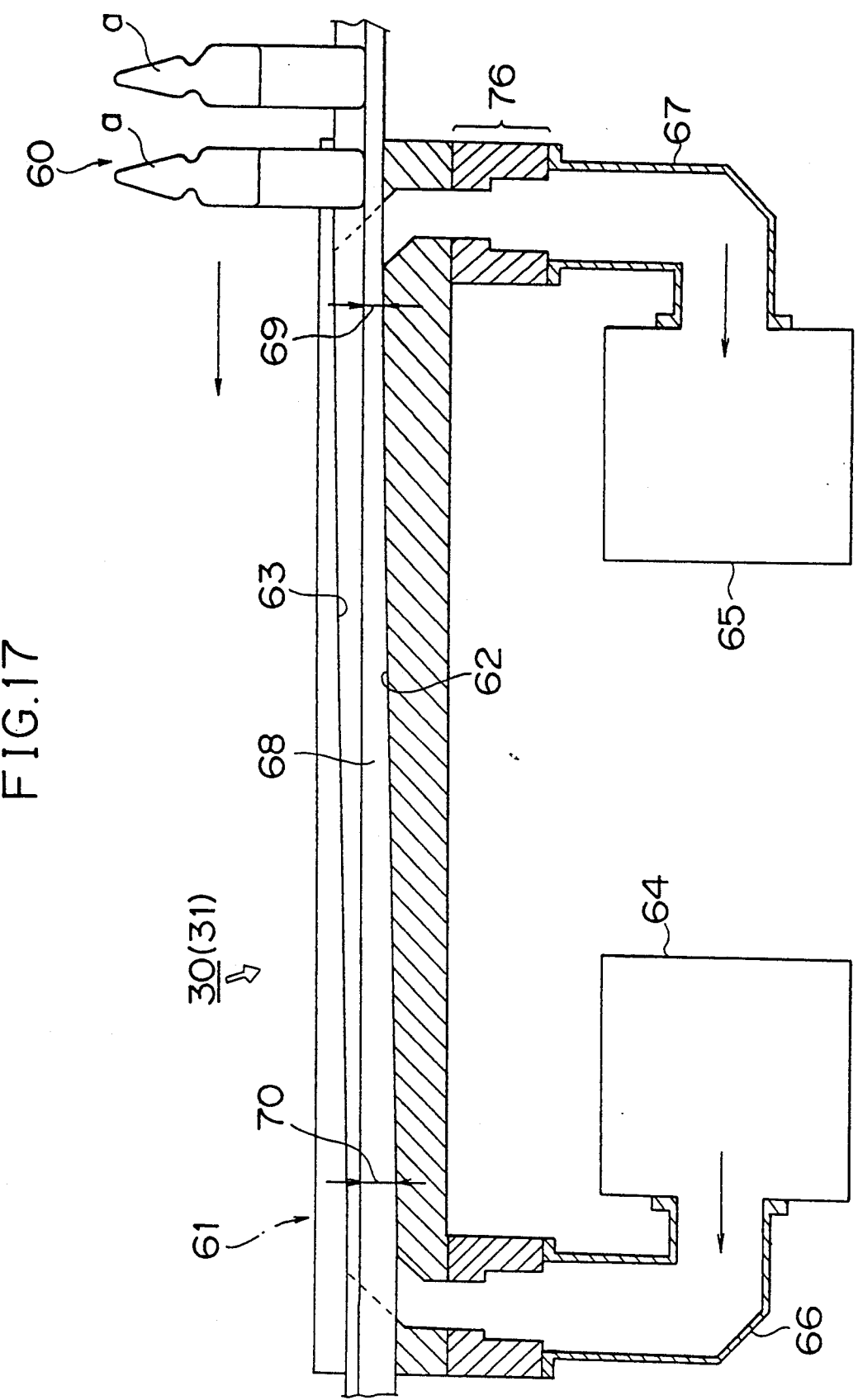
FIG. 17 is a front view showing, partially in a section, the square waveguide type microwave ovens of FIG. 16.

Referring to FIG. 17, reference numeral 60 designates an inlet side for the ampoules a into the oven and reference numeral 61 designates an outlet for the ampoules a from the oven. The ampoules a conveyed by the buckets 5 move in a direction as indicated by an arrow in FIG. 17 from right hand to left hand as viewed in FIG. 17. A floor 62 and a ceiling 63 of the microwave oven 30 slope downward from the inlet side 60 toward the outlet side 61 of the oven 30. Said floor 62 and said ceiling 63 define therebetween a pair of square waveguides 75, 75'. There are provided below the microwave oven 30 a microwave oscillator 64 which is connected by a waveguide 66 to the outlet side 61 and a microwave absorber 65 which is connected by a waveguide 67 to the inlet side 60 of the microwave oven 30, so that the microwave generated in the microwave oscillator 64 is propagated by the square waveguides 75, 75' along the upward slope from the outlet side 61 toward the inlet side 60 of the microwave oven 30. The direction in which the microwave is propagated is opposite to the direction in which the ampoules a are moved. Reference numeral 76 designates a caliber adjuster for the square waveguide.

A rail 68 is laid on the floor 62 of the microwave oven 30. The square waveguides 75, 75' extend on both sides of the rail 68 therealong and said rail 68 is formed from material which is nonabsorptive and transmissive for the microwave just like the rail 41 in the coaxial type oven so that the bottom of each ampoule a can be irradiated with the microwave propagated along the respective square waveguides 75, 75' and transmitted through the rail 68.

The rail 68 has U-shaped cross-section as in the case of the rail 41 previously described in reference with FIG. 11 and 12 and the ampoule a moved on the rail 68 with its bottom being in contact with the top surface thereof. Thickness of the rail 68 gradually increases from the oven inlet side 60 toward the oven outlet side 61 as will be apparent from FIG. 17 showing a thickness 69 of the rail 68 adjacent the oven inlet side 60 smaller than a thickness 70 thereof adjacent the oven outlet side 61.

Figure 16:
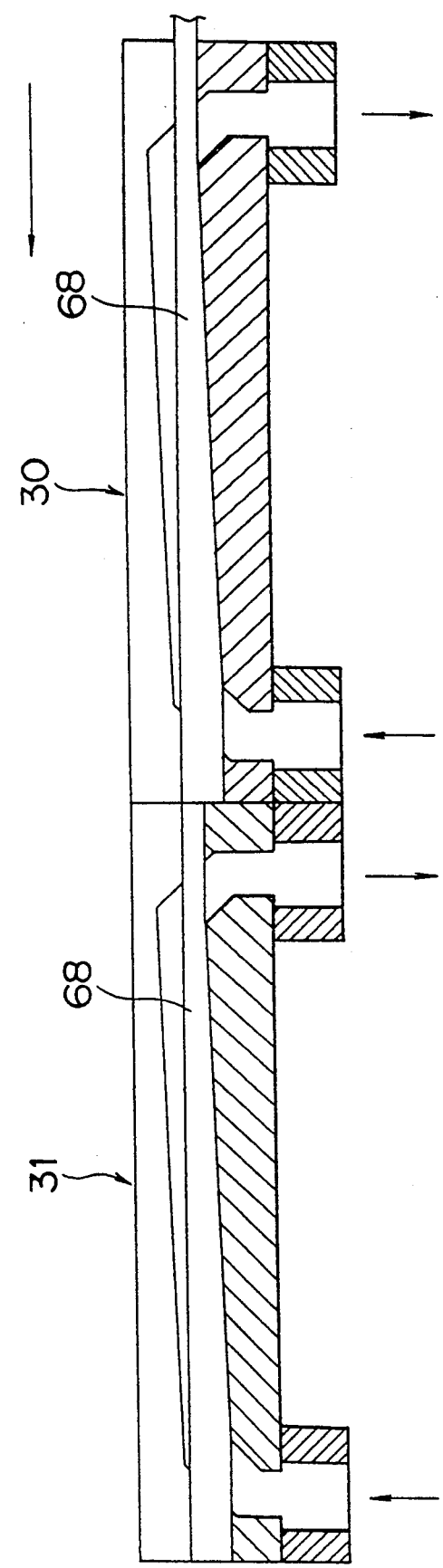
FIG. 16 is a sectional view of serially connected square waveguide type microwave ovens.

The microwave oven 30 as has been described above presents cross-sectional configurations on the oven inlet side 60 and the oven outlet side 61 as shown by FIG. 18 and 19, respectively. As shown, the oven 30 has a height 71 as measured from the oven's bottom 30' to the oven's floor 62 on the inlet side 60 and this height 71 is larger than a corresponding height 72 on the outlet side 61 of the oven 30. As has previously been explained in reference with FIG. 17, the rail 68 has the thickness 69 on the inlet side 60 less than the thickness 70 on the outlet side 61 of the oven 30. In this manner, the slope of the floor 62 and the thickness variation of the rail 68 offset each other so that the microwave oven 30 can provide a uniform depth 73 over an extent spanning from the inlet side 60 to the outlet side 61 of the oven 30 and thereby assure a horizontal surface along which the ampoules a move (see FIG. 16).

As will be seen in FIGS. 18 and 19, the instant embodiment of square waveguide type oven adopts a choke serving to absorb the microwave, similarly to the previously mentioned embodiment of the coaxial tube type oven.

Sterilization of the ampoules a is performed in the manner as has been described hereinabove and a subsequent handling is carried out using various means. Specifically, the sterilized ampoules a are successively taken by a star wheel 80 out from the respective buckets 5 and these sterilized ampoules a are then delivered by said star wheel 80 to a screw 81 which, in turn, feeds them onto a discharge tray 82. Reference numeral 83 designates an infrared radiation thermometer serving to take the temperature of the ampoules a having passed through the microwave ovens 30, 31.

The sterilizer of the invention operates in a following manner:

The ampoules a fed by the conveyor 3 into the hopper 1 are received in the helical groove of the screw 2 and carried to the star wheel 6 which, in turn, delivers the ampoules a successively into the recesses 9 of the respective buckets 5. During such delivery, the mechanism 4 assures that the ampoules a can be reliably delivered into the helical groove of the screw 2 even when they would not be properly engaged with the helical groove.

The ampoules a received by the buckets 5 are moved clockwise as viewed in FIG. 2 as the sprockets 14, 15 rotate and then preheated as they pass through the casing 20 dedicated for this purpose.

Preheating of the ampoules a advantageously economizes a dose of microwave irradiation required in the subsequent microwave ovens 30, 31. In addition, even if the temperature of the ampoules a is uneven depending on a particular storage condition of the ampoules a before they are carried into the sterilizer, passage through the preheat casing 20 heats the ampoules a up to a given temperature, minimizing the unevenness of temperature.

The ampoules a thus preheated by the casing 20 then pass through the microwave ovens 30, 31 and, during this process, the ampoules a have their bottoms or lower portions irradiated with the microwave. Medical fluid within the respective ampoules a absorbs the microwave energy, thereby is heated and sterilized. Such sterilizing effect is further enhanced by the hot air blast casing 21 adapted to heat-sterilizing the upper portion of each ampoule a passing therethrough.

There is a difference in operation between the cases in which the ampoules a pass through the coaxial tube type microwave oven and the waveguide type microwave oven, as will be described.

(A) COAXIAL TUBE TYPE

With the microwave oven of coaxial tube type, the dose of microwave irradiation for the ampoules a moving through the slots 54 of the respective ovens 30, 31 gradually increases from the oven inlet side 32 toward the oven outlet side 33 since the microwave is propagated by the inner conductor 38 from the oven outlet side 33 toward the oven inlet side 32. However, a degree of coupling between the medical fluid within each ampoule a and the microwave generally tends to decrease as the bottom of the ampoule a is spaced from the inner conductor 38. In this regard, the sterilizer of the invention is so constructed that the inner conductor 38 has the height 48 on the oven inlet side 32 which is larger than the height 49 on the oven outlet side 33 (as described in FIG. 9, FIG. 13 and FIG. 14) and thereby defines a slope and, consequently, the bottom of the ampoule a is more spaced from the inner conductor 38 on the oven outlet side 33 than on the oven inlet side 32. Within the respective microwave ovens 30, 31, therefore, said degree of coupling is relatively low on the oven outlet side 33 on which the dose of microwave irradiation is relatively high and said degree of coupling is relatively high on the oven inlet side 32 on which the dose of microwave irradiation is relatively low so that heating of the medical fluid within each ampoule a may be effected as gently as possible.

The rail 41 has the thickness 45 on the oven inlet side 32 less than the thickness 46 on the oven outlet side 33 and thus are gradually thickened from the oven inlet side 32 toward the oven outlet side 33 at a given ratio as has previously been described in reference with FIGS. 9 through 14. In this manner, the slope of the inner conductor 38 and the thickness variation of the rail 41 offset each other so that the microwave oven 30 can provide a uniform depth over an extent spanning between the oven inlet side 32 and the oven outlet side 33, assuring a horizontal surface along which the ampoules a are conveyed by the buckets 5.

(B) WAVEGUIDE TUBE TYPE

Also with the microwave oven of waveguide type, the dose of microwave irradiation for the ampoules a moving through the ovens 30, 31 gradually increases from the oven inlet side 60 toward the oven outlet side 61 since the microwave is propagated from the oven outlet side 61 toward the oven inlet side 60. In this waveguide type oven, however, the bottom of the microwave oven 30, i.e., the square waveguides 75, 75' slope downward from the oven inlet side 60 toward the oven outlet side 61 while the rail 68 is gradually thickened from the oven inlet side 60 toward the oven outlet side 61, as has already been explained in reference with FIGS. 16 through 19. As a result, the area of microwave irradiation for each ampoule a gradually decreases from the oven inlet side 60 toward the oven outlet side 61 so that, within the respective ovens 30, 31, the absorption efficiency may be relatively low on the oven outlet side 61 on which the dose of microwave irradiation is relatively high while said absorption efficiency may be relatively high on the oven inlet side 60 on which the dose of microwave irradiation is relatively low and thereby medical fluid within each ampoule a may be heated as gently as possible.

Just as in the case of coaxial tube type, the rail 68 is gradually thickened from the oven inlet side 60 toward the oven outlet side 61, define a slope, and this slope of the oven floor 62 and the thickness variation of the rail 68 offset each other so that the depth 73 of the oven 30 may be kept constant and the level at which the ampoules a are conveyed may be also kept constant.

Both in the coaxial tube type (A) and the square waveguide type (B), a pair of microwave ovens 30, 31 are serially connected to each other and such arrangement is advantageous in that the output of the microwave oscillators associated with the respective microwave ovens 30, 31 may be appropriately increased to obtain a total heating ability enough to achieve a gentle but effective sterilization of the ampoules a even when they contain therein a relatively large volume of medical fluid, since said medical fluid is two-stepwise heated.

The temperature of the ampoules a having been sterilized by passage through the microwave ovens 30, 31 and the hot air blast casing 21 is measured by the infrared radiation thermometer 83. Thereafter, the ampoules a are carried by the buckets 5 into the casing 22 for heat insulation.

Upon completion of the sterilizing process, the ampoules a are taken by the star wheel 80 out from the buckets 5 and then conveyed by the screw 81 onto the discharge tray 82.

Through the specific embodiment shown adopts a pair of serially connected microwave ovens 30, 31, three or more, for example, six or ten serially connected microwave ovens may be adopted.

While the invention has been particularly shown and described with reference to preferred embodiment thereof, it will be understood by those skilled in the art that the foregoing and other changes in form and details can be made therein without departing from the spirit and scope of the invention.

What is claimed is:

1. A sterilizer for sterilizing the contents of sealed containers, comprising:
   (1) an oven having an inlet side and an outlet side;
   (2) a microwave propagation means disposed within the oven such that the propagation means has a constant declining slope from adjacent the inlet side to adjacent the outlet side; and
   (3) a support rail disposed in the oven having a substantially horizontally-disposed support surface for supporting a bottom portion of the container such that the container is substantially horizontally movable through the oven and the degree of coupling of microwaves with the contents of the container gradually increase from adjacent the outlet side to adjacent the inlet side.

2. Sterilizer as recited in claim 1 wherein the microwave propagation means is a coaxial tube microwave generator and an inner conductor thereof has a constant declining slope from adjacent the inlet side to adjacent the outlet side.

3. Sterilizer as recited in claim 2, wherein the inner conductor has a constant declining slope from the inlet side toward the outlet side and the support rail is laid on the top of the inner conductor.

4. Sterilizer as recited in claim 3, wherein said support rail is gradually thickened from the inlet side toward the outlet side.

5. Sterilizer as recited in claim 4, wherein said support rail is thickened from the inlet side toward the outlet side of the oven at a constant ratio.

6. Sterilizer as recited in claim 5, wherein said support rail defines a U-shaped groove serving to hold the bottom portion of the sealed container.

7. Sterilizer as recited in claim 2 wherein a slot is formed in a top portion of an outer tube of the coaxial tube microwave generator for receiving a portion of the container and allowing the container to be substantially horizontally movable through the oven.

8. Sterilizer as recited in claim 2 wherein the degree of coupling of the microwaves with the contents of the container gradually increases from adjacent the outlet side to adjacent the inlet side at a constant ratio.

9. Sterilizer as recited in claim 1 wherein a bucket moves the sealed containers through the oven.

10. Sterilizer as recited in claim 9 wherein the bucket has a bucket arm engageable at a forward end thereof with the containers and at a base end thereof with a bucket rail.

11. Sterilizer as recited in claim 10 wherein the forward end has recesses for receiving the containers.

12. Sterilizer as recited in claim 10 wherein the base end has rollers engageable with the bucket rail.

13. Sterilizer as recited in claim 12 wherein a roller is engageable with opposite sides of the bucket rail.

14. Sterilizer as recited in claim 10 wherein the base end of the bucket arm has a centrally-disposed upstanding projection.

15. Sterilizer as recited in claim 14 wherein the projection is engageable with a sprocket for moving the bucket arm.

16. Sterilizer as recited in claim 15 wherein the base end has a disc which is engageable with a disc of a next adjacent bucket arm such that rotation of the sprocket causes a succession of bucket arms and the containers therein to be moved along said support rail.

17. Sterilizer as recited in claim 1 wherein the microwave propagation means is a square waveguide and the square waveguide has a constant declining slope from adjacent the inlet side to adjacent the outlet side.

18. Sterilizer as recited in claim 17, wherein the support rail is laid on a floor of the oven, with the support rail being gradually thickened from the inlet side toward the outlet side.

19. Sterilizer as recited in claim 17 wherein a slot is formed in a top portion of the square waveguide for receiving a portion of the container and allowing the container to be substantially horizontally movable through the oven.

20. Sterilizer as recited in claim 17 wherein the degree of coupling of the microwaves with the contents of the container gradually increases from adjacent the outlet side to adjacent the inlet side at a constant ratio.

21. Sterilizer as recited in claim 1 wherein there are two or more serially connected ovens, and each of the sealed containers moved through these two or more ovens receive a dose of microwave irradiation which is less than the dose required by a single oven to heat the contents of the container to the same temperature.

22. Sterilizer as recited in claim 1 wherein the degree of coupling of the microwaves with the contents of the container gradually increases from adjacent the outlet side to adjacent the inlet side at a constant ratio.

* * * * *